United States Patent [19]

Giurtino et al.

[11] Patent Number: 5,252,090
[45] Date of Patent: Oct. 12, 1993

[54] SELF-LOCKING IMPLANTABLE STIMULATING LEAD CONNECTOR

[75] Inventors: Joel F. Giurtino, Engelwood; Ian A. Adamson, Denver, both of Colo.

[73] Assignee: Telectronics Pacing Systems, Inc., Englewood, Colo.

[21] Appl. No.: 954,122

[22] Filed: Sep. 30, 1992

[51] Int. Cl.$^5$ ............................................. H01R 4/24
[52] U.S. Cl. .................................... 439/441; 607/9
[58] Field of Search ............................ 439/436–441

[56] References Cited

U.S. PATENT DOCUMENTS

| | | | |
|---|---|---|---|
| 4,848,346 | 7/1989 | Crawford | 128/419 P |
| 4,942,876 | 7/1990 | Gotthardt | 128/419 P |
| 4,995,389 | 2/1991 | Harris | 128/419 P |
| 5,069,209 | 12/1991 | Posin | 128/419 P |

OTHER PUBLICATIONS

Calfee et al., "A Voluntary Standard for 3.2 mm Unipolar and Bipolar Pacemaker Leads and Connectors", Pace, vol. 9, pp. 1181–1185, Nov.–Dec. 1986, Part II.

International Standard IS-1, International Organization for Standardization document ISO/DIS 5841-3, 1989.

Primary Examiner—Joseph H. McGlynn
Attorney, Agent, or Firm—Gottlieb, Rackman & Reisman

[57] ABSTRACT

A connector assembly for an implantable stimulating device employs a lead-locking spring clip to reliably provide a mechanical and electrical connection between the terminal pin of an electrode lead and the device, while reducing the user interaction required during implantation and disconnection. No tools are required to establish the connection. No user action, other than inserting the lead into the connector, is necessary to lock the lead into place. Disconnecting the lead requires only the application of a modest transverse compressing force to a release button on the connector assembly. In the event that a withdrawal force is applied to the lead without simultaneously applying the compressing force to the release button, the connector assembly increases its holding force on the electrode lead.

32 Claims, 7 Drawing Sheets

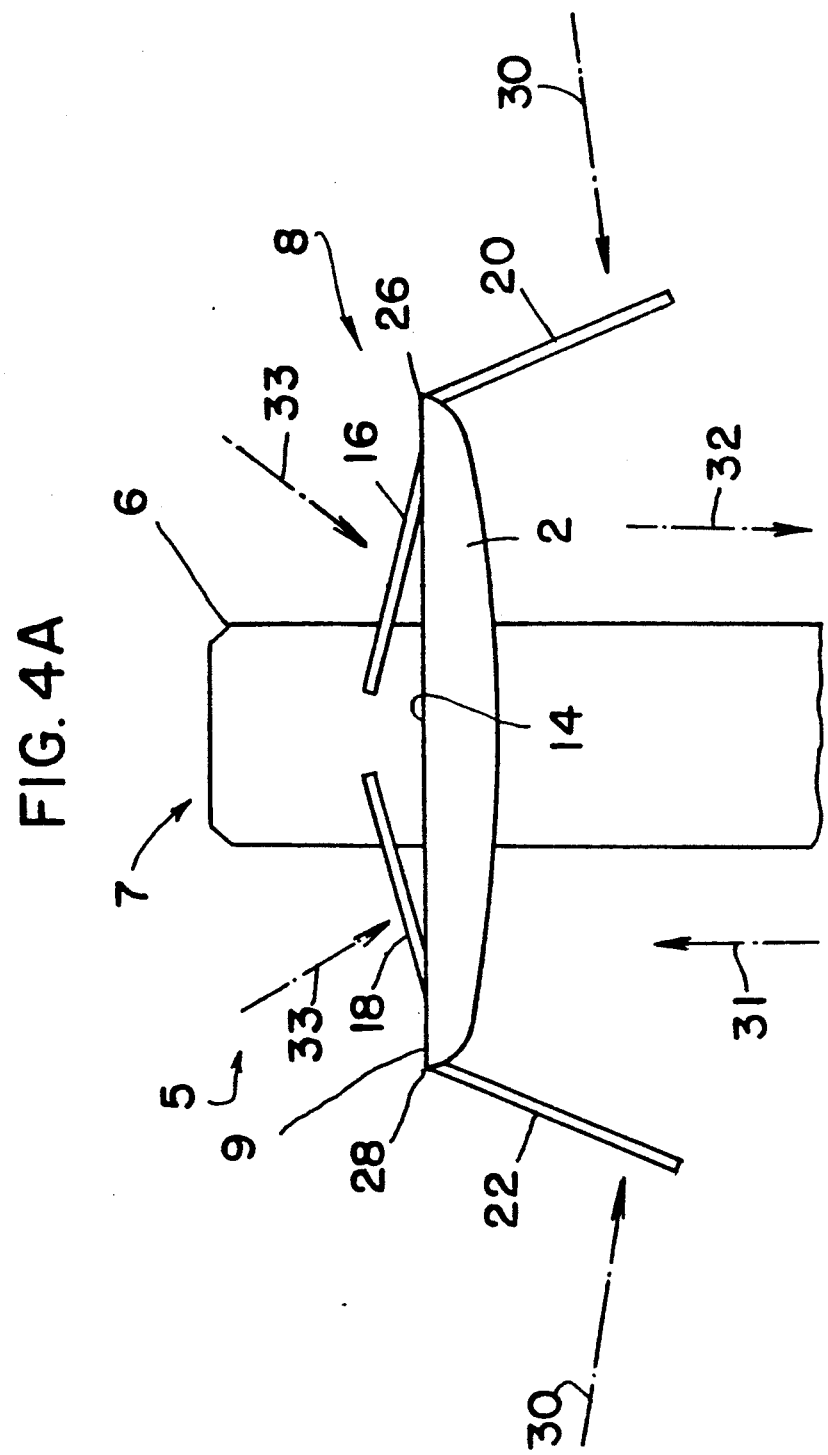

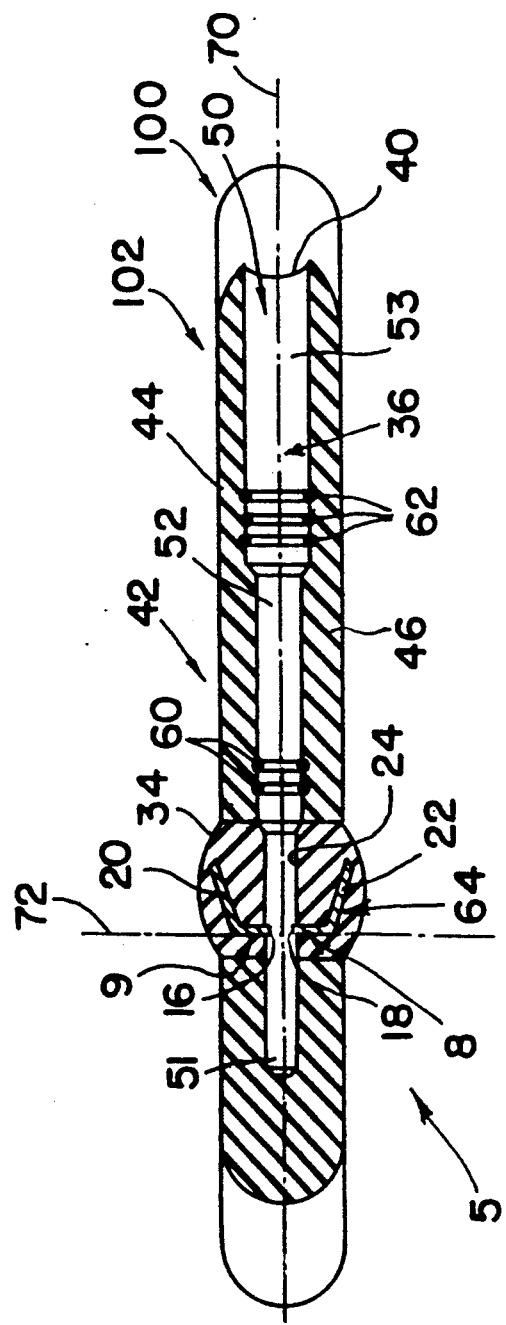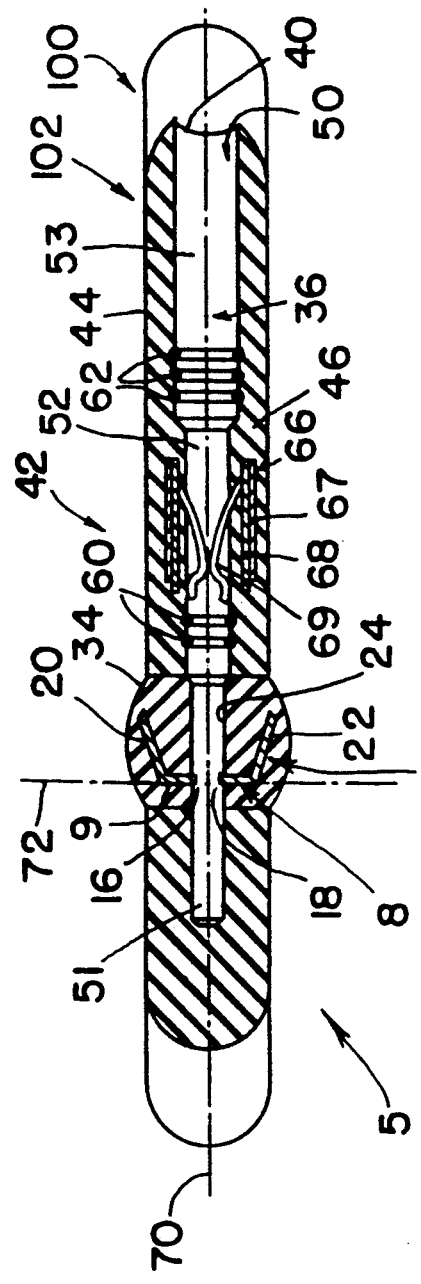

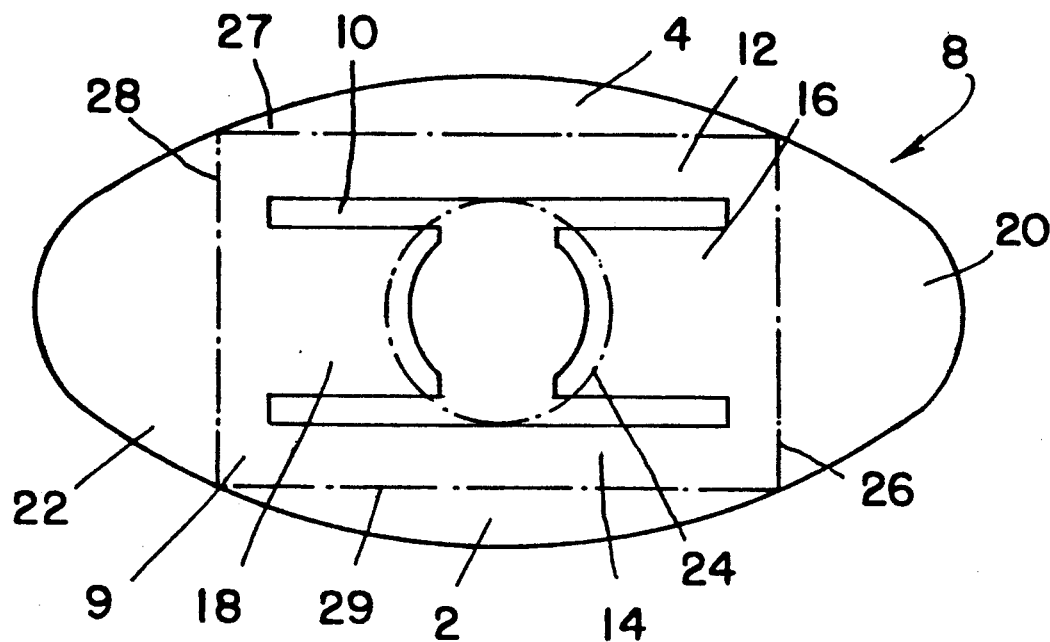
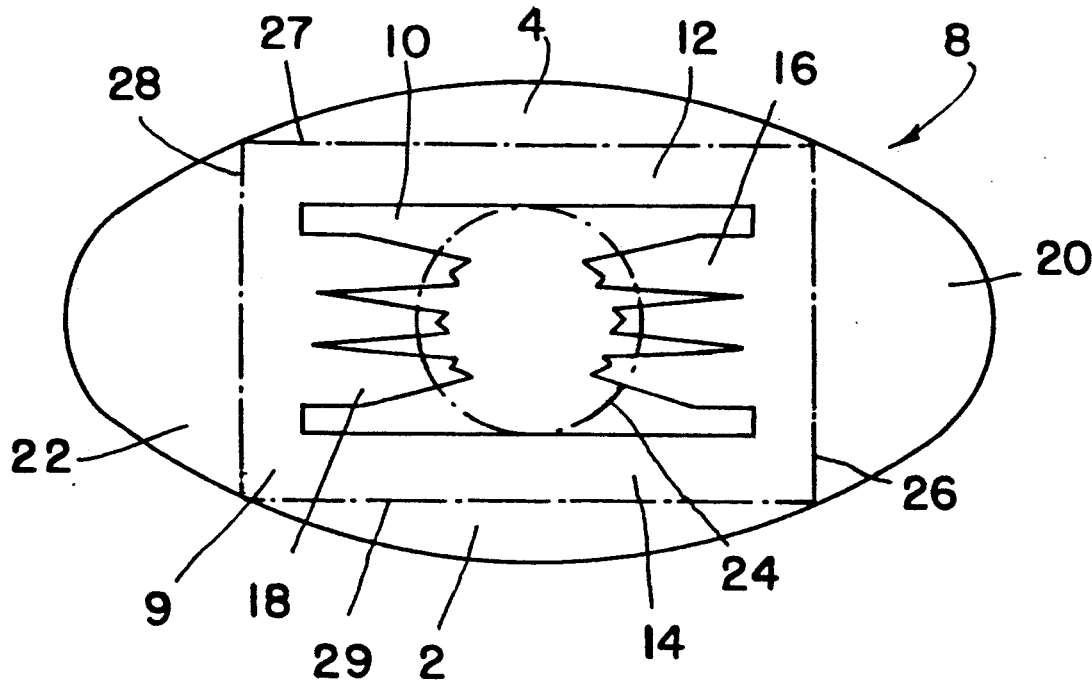

SELF-LOCKING IMPLANTABLE STIMULATING LEAD CONNECTOR

TECHNICAL FIELD

This invention relates to a connector assembly for attaching an implantable stimulation lead to an implantable stimulator, and more particularly to a connector assembly that allows a lead to be easily, yet reliably, connected to and disconnected from the stimulator.

BACKGROUND OF THE INVENTION

A pacing system includes a pacemaker, comprising a case which contains electronic circuitry and a power supply, and a pacing lead. A distal end of the lead interfaces with a patient's heart to deliver electrical pulses generated by the pacemaker and to provide for sensing of cardiac electrical signals. The proximal end of the lead connects to input/output terminals of the pacemaker, which are located within an external connector component of the pacemaker. A lead connector for a cardiac stimulator requires a mechanical fixation to prevent separation of the lead(s) from the pacemaker. In current commercial cardiac stimulation devices, set screws are almost universally used to accomplish such mechanical fixation. This requires additional equipment (e.g., a screwdriver) to actuate the screw. The connector assembly of the present invention utilizes a device that is easy to use and requires no additional equipment for it to work.

In a pacing system comprising a single or multiple electrode lead and a pacemaker, the distal portion of the lead holds the electrodes, which are normally placed in the right ventricle or right atrium of the heart Insulated helical coiled wire conductors connect to the electrodes to carry, along the length of the lead, physiological electrical signals from the heart to the pacemaker and pacing pulses from the pacemaker to the heart. A terminal pin is physically affixed to the proximal end of the lead, making electrical contact with the conductors within the lead The terminal pin is inserted into a socket in the connector area of the pacemaker, where the terminal pin contacts an electrical connector jack within the socket, serving as an interface between the lead conductor and electronic circuitry within the pacemaker. This connection between the terminal pin and the jack must provide for a simple, long-term safe and secure, yet detachable, connection.

The connector assembly commonly is in the form of male and female connectors, with the terminal pin at the proximal end of the pacing lead serving as the male connector. When these connectors are joined, a reliable and constant electrical contact must be maintained between the electrical conductors in the lead and the pacemaker. This connection must be secure so that the lead does not disconnect during use and is completely sealed from body fluids. However, the connection must be detachable to allow for replacement of the pacemaker or lead.

Heretofore, various connectors have been used to connect the terminal pin at the proximal end of a lead to the electrical connector jack in the socket of a pacemaker. A common connector system uses a miniature socket head set screw to secure the terminal pin to the electrical connector jack inside the socket and to provide the necessary electrical contact. When this type of connector system is employed, an implanting physician must tighten the set screw after the terminal pin of the lead is in place within the neck of the pacemaker during implantation within a patient. This procedure is difficult due to the small size of the screw and the inconvenient working conditions of the operating room. In these circumstances, the set screw may protrude into the bore of the connector socket such that it blocks the proper insertion of the pacemaker lead. Furthermore, the set screw socket or threads may be stripped due to overtightening. Another problem that may result from overtightening the screw is that the screw may bear against the outer ring of the lead termination sufficiently hard that it deforms the ring and prevents its removal from the connector socket, requiring removal of both the lead and pacemaker when replacement of the pacemaker alone would normally be desired. In addition, when an Allen wrench is inserted into the header to rotate the set screw, body fluids generally are allowed to enter the connector through the wrench seal. Furthermore, the usage of set screws is disadvantageous in that body fluids cause deterioration of a screw over time, allowing fluids to enter into the electrical contact area and resulting in circuit damage and malfunctioning.

One alternative to set screw connectors is a connector system employing various types of spring contacts in the form of small fingers which contact the lead terminal pin. The primary disadvantages of such connectors are poor mechanical contacts between leads and sockets and a suboptimal intermittent electrical contact, rather than a contact over a large surface area.

In U.S. Pat. No. 4,848,346, entitled "Pacemaker Connector System", issued to K. F. Crawford on Jul. 18, 1989, there is described a pacemaker connector system for a bipolar pacemaker, employing circular springs in each of two connector block assemblies, which circumferentially grip the central and outer terminals of a coaxial heart lead. Each of the springs has an extension arm which protrudes beyond the bounds of a pacemaker header assembly. The protruding extension arms, each of which is covered by rubber septum buttons to prevent invasion by body fluids, may be depressed to open the interior of the spring and allow insertion of the lead therein.

U.S. Pat. No. 4,942,876, entitled "Pacemaker Terminal Apparatus", issued to G. R. Gotthardt on Jul. 24, 1990, discloses a pacemaker terminal for connecting a terminal pin of a pacing lead, the terminal consisting of a two sections, a first section fixed to the pacemaker and a second section movably engaged with the first section. A spring element is interposed between the two sections to exert a force tending to displace the moveable section from the fixed section. Both sections are perforated by transverse holes which, upon application of squeezing pressure to the terminal to overcome the spring action, become aligned to allow insertion of the lead terminal pin into the holes. Upon release of the squeezing pressure, the spring element displaces the sections to capture the lead terminal pin securely in the holes. The holes may have an internal thread, for example having an asymmetric sawtooth pattern, to further hold the lead in place and maintain electrical contact.

U.S. Pat. No. 4,995,389, entitled "Multielectrode Quick Connect Cardiac Pacing Lead Connector Assembly", issued on Feb. 26, 1991 to D. L. Harris, teaches a multiple electrode lead connector assembly for connecting a plurality of insulated conductor feedthroughs, extending from a pacemaker case into a soft and pliable neck area, to a specific electrode of a multi-electrode pacing lead. The connector is flexible and consists of a plurality of U-shaped spring electrical contacts, each having a bight and two upstanding legs for contacting ring contacts at the proximal end of the pacing lead. The pacemaker neck has a lumen with a closed proximal end and an open distal end which receives the multielectrode pacing lead. The upstanding legs of the U-shaped spring electrical contacts straddle the lumen of the neck in a position to flexibly engage and grip a respective ring contact on the pacing lead.

As indicated earlier, a disadvantage of connectors which employ Allen set screws to secure a pacing lead is that the aperture for entry by the wrench for turning the screw and securing the lead has a tendency to leak body fluids into the internal circuits. A further disadvantage of these connectors is the requirement for special tools and procedures for securing the lead. In a surgical clinical environment, securing a lead in this manner is highly awkward, inefficient and possibly dangerous to the patient. Similarly, although the spring contacts of the aforementioned patents avoid the necessity of special tools, they still require the surgeon to manipulate an engaging device, such as switches, buttons or levers, while securing the lead. Furthermore, these spring contacts require the surgeon to engage the lead by applying a significant insertion force. It is desirable to improve the efficiency of the implant operation by requiring less manipulation of engaging devices and the application of a smaller insertion force to engage the lead into the implantable stimulation device.

A significant disadvantage of some of the prior art connectors which employ spring contacts is their frequent inability to maintain an adequate holding force on the lead over the useful lives of the pacer and lead. Furthermore, in addition to the holding force of prior art spring contact connectors being inadequate, the insertion force required to assemble them is often inappropriately high. Accordingly, it is desirable to reduce the force of entry, or insertion force, of the terminal pin into the header jack of a spring contact connector. Moreover, it is critical to improve the holding force of connectors which employ an engaging mechanism utilizing spring contacts.

It is, therefore, a primary object of the present invention to provide a spring contact connector that requires only a low insertion force but has a high holding force.

It is another object of the present invention to provide for reliable connection of electrode leads to an implantable stimulation device, such as a pacemaker or neurostimulator, while optimizing ease of connection for the surgeon at the time of implantation, by requiring no manipulation of engaging devices or tools and by requiring minimal insertion force to engage the terminal pin of the lead with the connector jack of the implantable stimulation device.

It is a further object of the present invention to provide a connector for an implantable stimulation device which is "self-locking" in that it responds to the application of a withdrawal force on a lead by increasing its holding force upon the lead.

A still further object of the present invention is to provide the capability in a connector assembly for the electrical jack thereof to automatically secure and make electrical contact with the terminal pin of an implantable stimulation lead.

It is yet another object of the present invention to provide a connector assembly in which no tools, implements or other supporting equipment is required to release a lead from an implantable stimulation device.

A further object of the present invention is to provide a connector assembly in which no body fluid path is formed in the locking mechanism thereof.

An additional object of the present invention is to provide a connector which employs a spring contact embedded within a silicone rubber release button, or plug, which promotes stiffness and support to the spring contact, provides precise alignment of the spring within a connector housing and effectively seals the housing against intrusion of body fluids.

The connector of the present invention is a simple apparatus for lead attachment that provides the requisite mechanical and electrical connection functions, using fewer components and less labor in implementation, yet providing higher reliability, durability, resistance to breakdown due to reactions with body fluids, a small size, and efficiency in manufacture.

SUMMARY OF THE INVENTION

Briefly stated, and in accordance with one embodiment of the present invention, there is provided a connector assembly for detachably connecting a terminal pin of an electrical lead to an electrical device. The assembly comprises a connector housing of insulating material that is carried by the electrical device, with the housing including an elongated lumen therein having a closed proximal end and an open distal end which receives the electrical lead. The assembly further includes a generally U-shaped electrically conductive spring clip positioned within the housing and having first and second spaced apart leg portions extending alongside respective opposite sides of the lumen, a base portion extending between the leg portions generally transversely of the lumen, and first and second jaw members extending generally toward one another transversely of the lumen and having end portions thereon terminating at spaced apart locations within the lumen The spacing between the end portions is less than the width of the terminal pin so that the jaw members are adapted to grip the terminal pin upon insertion of the terminal pin into the lumen, and the U-shaped spring clip and the housing are constructed and arranged so that upon application of a compressive force to opposite sides of the housing, adjacent to the first and second leg portions, the first and second jaw members move away from one another, increasing the separation of the end portions thereof to a spacing greater than the width of the terminal pin and facilitating withdrawal of the terminal pin from the lumen.

In accordance with another aspect of the present invention, the leg portions, base portion and jaw members of the resilient spring clip may be integral with one another.

In accordance with yet another aspect of the present invention, the jaw members of the resilient spring clip may be carried by the base member thereof and may be coplanar to the base member when the spring clip is in a relaxed condition, out of engagement with a terminal pin, with the jaw members flexing out of the plane of the base member when engaged by a terminal pin.

In accordance with a still further aspect of the present invention, the jaw members may grip the terminal pin with a retaining force when engaged by the terminal pin which, in the absence of a compressive force on the leg portions of the spring clip, increases upon application of a withdrawing force to the terminal pin.

In accordance with an additional aspect of the present invention, the base member of the resilient spring clip may include a pair of integral reinforcing flanges positioned perpendicularly to the plane of the base member and in spaced apart relation to one another.

BRIEF DESCRIPTION OF THE DRAWINGS

While the specification concludes with claims particularly pointing out and distinctly claiming the subject matter of the invention, it is believed that the invention will be better understood from the following description, taken in conjunction with the accompanying drawings, in which:

FIG. 4A is a side elevation view of the resilient metallic spring clip of FIG. 2, illustrating penetration of the spring clip aperture by the terminal pin of an implantable stimulation lead;

FIG. 5 is an enlarged sectional view, taken along the line 5—5 of FIG. 1, showing a connector assembly for connecting a unipolar lead to an implantable stimulation device;

FIG. 6 is a sectional view, similar to that shown in FIG. 5, showing a connector assembly for connecting a bipolar lead to an implantable stimulation device;

FIG. 9 is a top plan view of a sheet metal blank, perforated by an aperture but not yet bent into final form, which is used to construct a resilient metallic spring clip having jaws with internally radiused teeth, such as those shown in FIG. 7; and, FIG. 10 is a top plan view of a sheet metal blank, perforated by an aperture but not yet bent into final form, which is used to construct a resilient metallic spring clip having jaws with multiple teeth;

DESCRIPTION OF THE PREFERRED EMBODIMENT OF THE INVENTION

Figure 1:
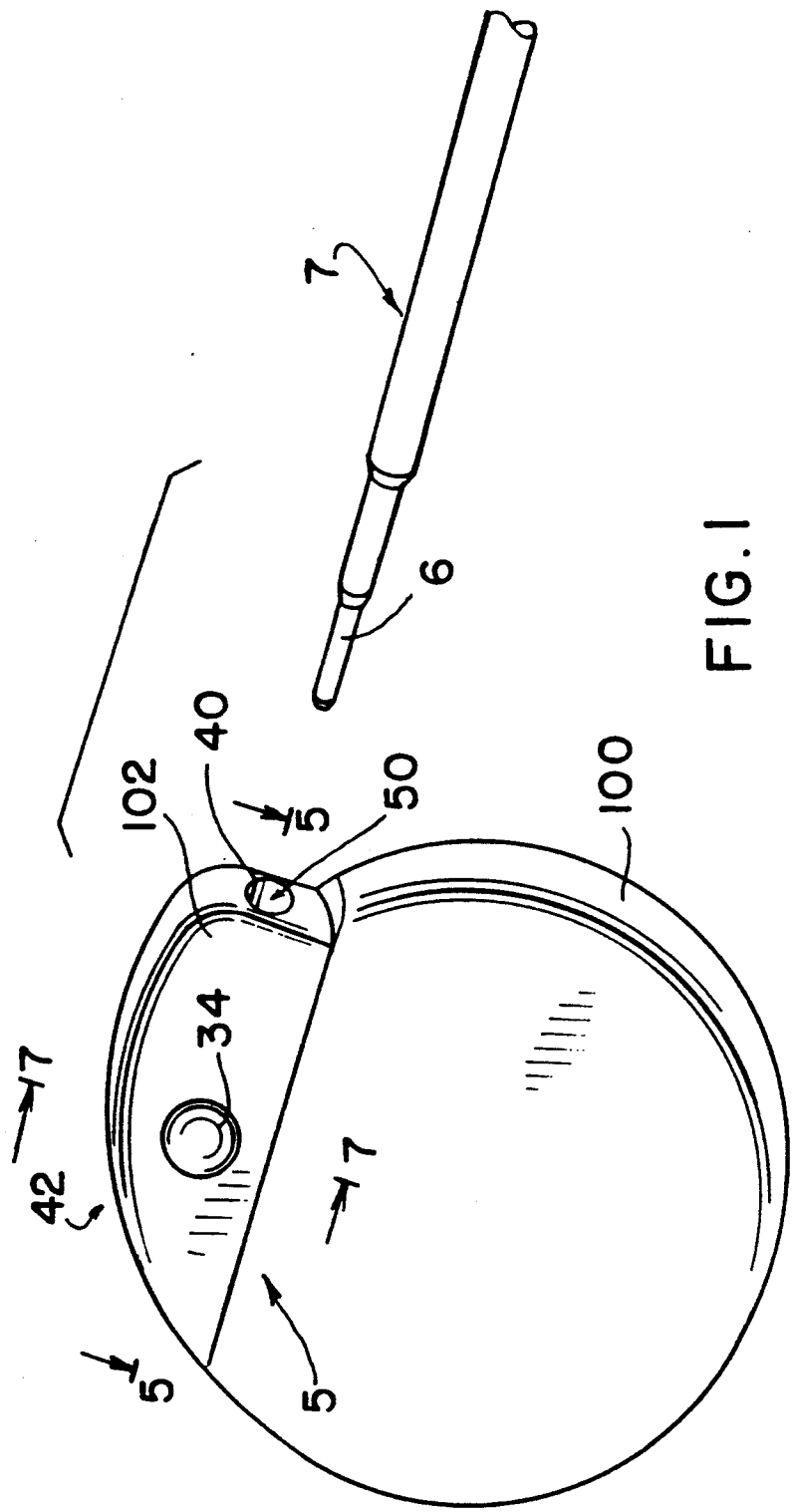
FIG. 1 is a perspective view of an implantable stimulation device embodying a lead connector assembly in accordance with the present invention.

FIG. 1 is a perspective view of an implantable stimulation device or stimulator 1 having a connector assembly in accordance with the present invention, shown generally at 5, for connecting the terminal pin 6 of a stimulation or electrode lead 7 to the stimulator. The connector assembly 5 is incorporated in a neck assembly 42 fixedly carried on a case 100 of the stimulator 1. The connector assembly 5 includes a resilient release button, shown at 34, that is carried in and extends through housing or wall 102 to opposite sides of the neck assembly 42. The button 34 is employed in releasing the electrode lead from the grasp of the connector assembly, as will be described in greater detail hereinafter. The neck assembly 42 also includes an opening 40 into which the terminal pin of the electrode lead may be inserted to effect an electrical connection between the lead and the stimulation device.

Figure 2:
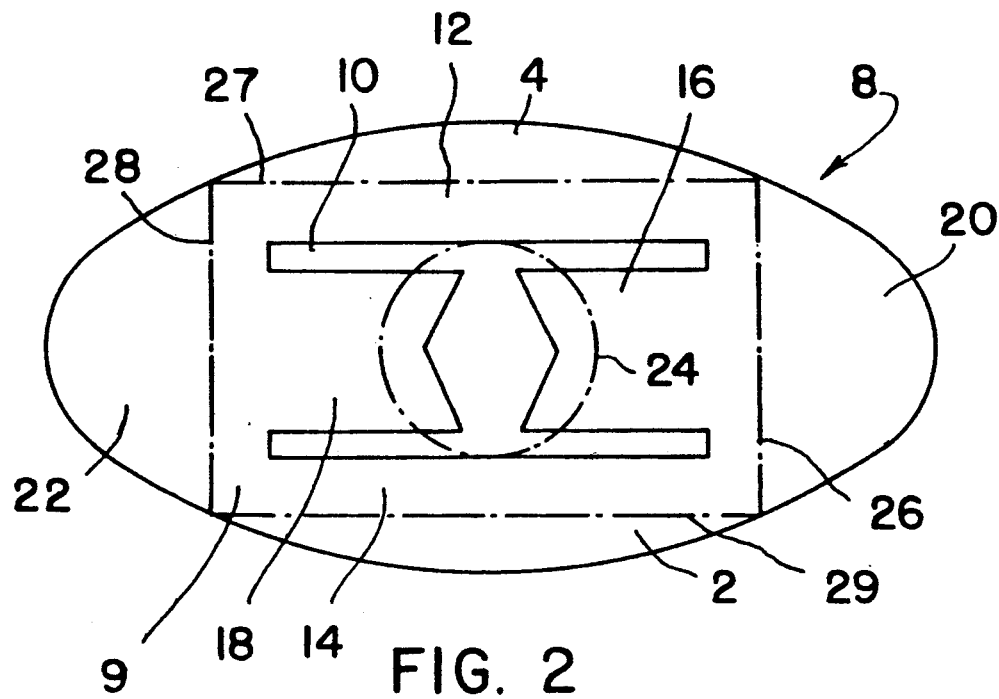
FIG. 2 is a top plan view of a sheet metal blank, perforated by an H-shaped aperture but not yet bent into final form, which is used to construct a resilient metallic spring clip that is employed in the connector assembly of the present invention.
Figure 3:
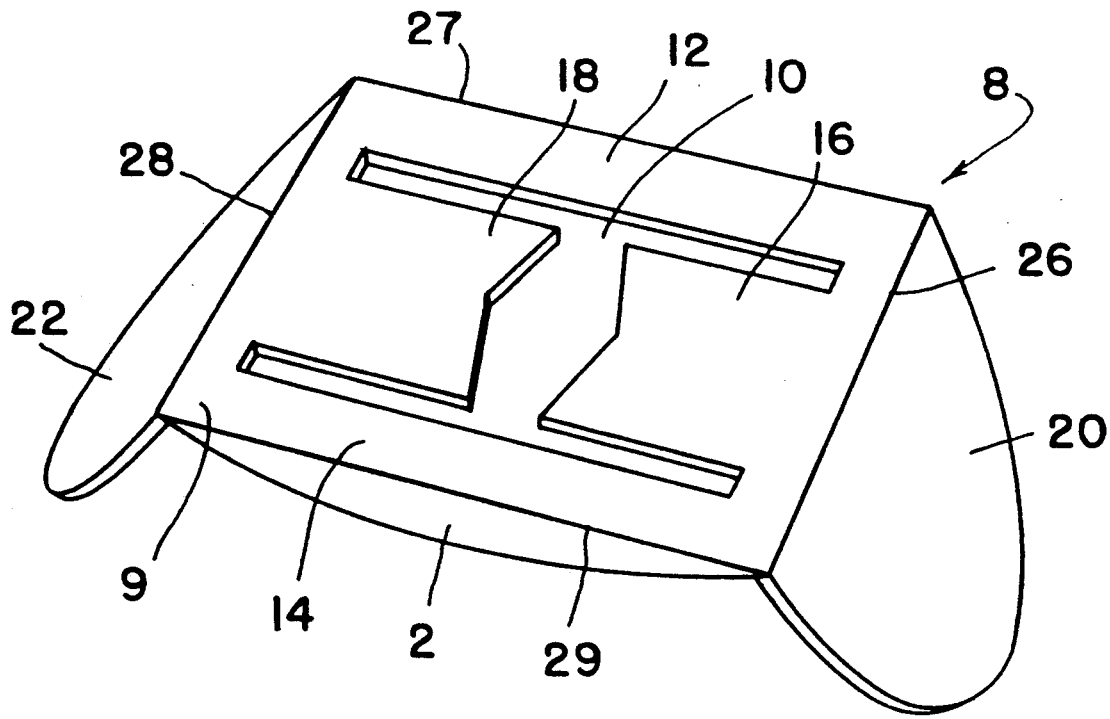
FIG. 3 is a perspective view of the sheet metal blank shown in FIG. 2, after it has been bent into the shape of the resilient metallic spring clip.

FIGS. 2, 3 and 4A show various views of a resilient metallic spring clip 8 that is utilized in the connector assembly 5 of the present invention. The metallic spring clip 8 is used both to provide a self-locking arrangement that holds the electrode lead 7 in place and to serve as an electrical jack or contact between the implantable stimulation device 1 and the terminal pin 6 (FIG. 4A) of electrode lead 7. The spring clip 8 is preferably prepared from a resilient, high strength, corrosion resistant, biocompatible material, such as tempered stainless steel. The spring clip 8 may be stamped or cut from a single sheet of metal or, to provide a stronger spring clip, made from a composite structure of multiple laminated leaves of sheet metal. The preferred embodiment of the spring clip 8 includes multiple laminated layers of sheet metal to provide for a thin, small and light connector assembly 5 which will maintain a good holding force, shown by an arrow 33, on terminal pin 6.

The preferred embodiment of the spring clip 8 is prepared from a planar, pre-cut metallic blank having an elliptical shape, as shown in FIG. 2, which is then bent into the U-shaped form shown in FIG 3. However, the spring clip 8 may also be formed from pre-cut blanks having other shapes, such as rectangles, squares, circles and other configurations, which may or may not have a symmetric shape. Referring to FIG. 3, spring clip 8, after being bent into shape, comprises a U-shaped spring clip having a base member or portion 9 which extends between first and second leg members or portions 20 and 22, respectively. The base portion 9 includes first and second spring members 12 and 14, respectively, therein and carries a pair of spaced apart jaw members or jaws 16 and 18 thereon which extend generally toward one another. The members 12, 14, 16 and 18 define a central aperture 10 in base portion 9. The preferred form of the aperture 10 is an H-shape, although many other shapes are possible, provided that such shapes allow for the definition of the required elements of spring clip 8. The aperture 10 encompasses and is aligned with a generally circular area or opening 24 (FIG. 2) which corresponds to the cross-sectional area of the terminal pin 6 (FIG. 4A), as well as the terminal pin receiving portion 51 of a lumen or lead cavity 50 (FIG. 5). The distal end of lumen 50 terminates in the opening 40 of neck assembly 42.

Referring to FIGS. 1-4A, the aperture 10 is cut into the spring clip 8 so as to be in alignment with the generally circular opening 24 in order to accept penetration by the terminal pin 6 of an implantable stimulating lead 7. Each jaw 16 and 18 of the pair of jaws is positioned directly opposite its paired jaw in the circular opening 24 so that the jaws flex and firmly engage the terminal pin of the implantable stimulating lead when the terminal pin is inserted therebetween. In addition, the spring members 12 and 14 also flex to enhance the engagement between the jaws and the terminal pin. Moreover, the retaining force 33 on the terminal pin 6 of the implantable stimulating lead 6 increases when a transverse withdrawal force 32 is applied to the lead. The spring members 13 and 14 provide sufficient force to initially engage the jaws 16 and 18 around a terminal pin 6 inserted into the circular opening 24 over a full range of tolerances in terminal pin diameter so as to sustain a holding force 33 of at least 2 lb. on the terminal pin. When not deflected by a terminal pin 6, the metallic jaws 16 and 18 and the spring members 12 and 14 are all preferably positioned within a common plane 72 (FIG. 5) that is perpendicular to the longitudinal axis 70 of the lumen 50.

Figure 7:
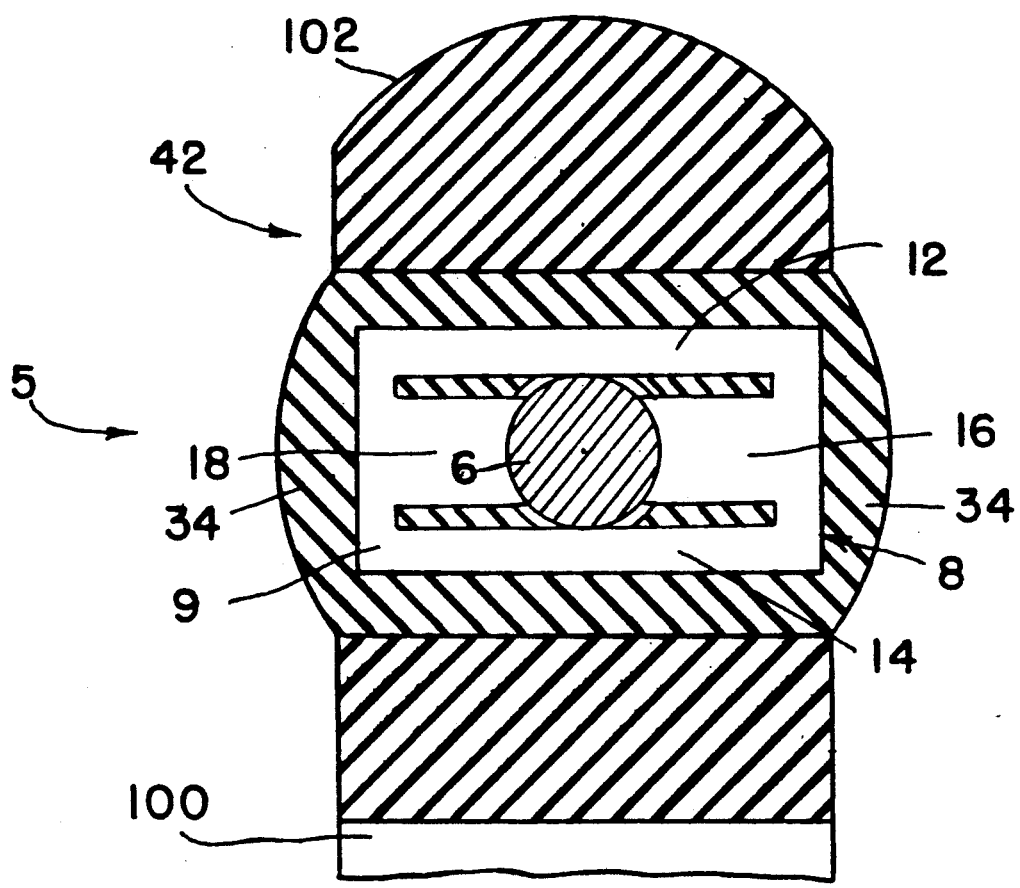
FIG. 7 is an enlarged sectional view, taken along the line 7—7 of FIG. 1, showing a connector assembly in which an alternate jaw arrangement is utilized in the resilient spring clip.
Figure 8:
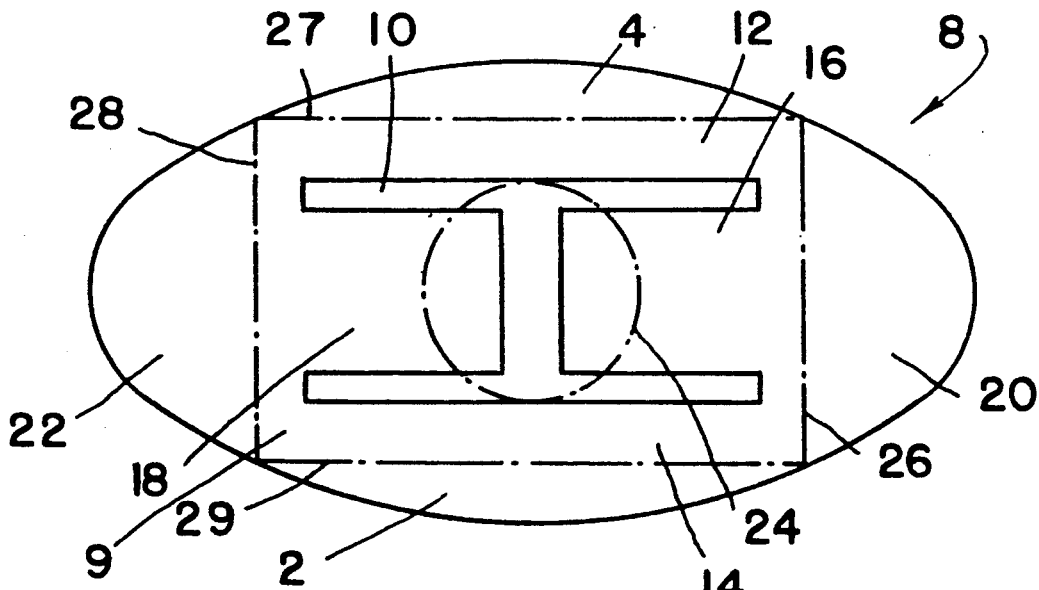
FIG. 8 is a top plan view of a sheet metal blank, perforated by an aperture but not yet bent into final form, which is used to construct a resilient metallic spring clip having jaws with flat teeth.

In the preferred embodiment of the invention, the jaws 16 and 18 of spring clip 8 have V-shaped end portions or teeth. In other embodiments of the invention, the end portions of the jaws may take other shapes, such as flat teeth (shown in FIG. 8), internally radiused teeth (see FIGS. 7 and 9) or multiple teeth (see FIG. 10). The material used to construct the spring clip 8 must be sufficiently hard that the jaws will maintain their geometric integrity while grasping the terminal pin 6.

Referring to FIGS. 1, 2, 3 and 4A, the resilient metallic U-shaped spring clip 8 includes two (or more) leg portions 20 and 22, as indicated earlier. Leg portions 20 and 22 extend distally from the base portion 9 and are bent along bend lines 26 and 28 to form a high angle (e.g., 45° to 90°) with the plane of the base portion 9 of the spring clip, as is illustrated in the side elevation view of the spring clip in FIG. 4A. The leg portions 20 and 22 have a length, relative to the length of the spring members 12 and 14 and the jaws 16 and 18, that allows adequate clearance for the leg portions to fit within the neck assembly 42 of the implantable stimulator, while providing for sufficient displacement of the jaws, relative to the circular opening 24, for the jaws to clear the largest terminal pin 6 allowed under industry standards (Voluntary Standards VS-1 and VS-1B, Calfee et al., "A Voluntary Standard for 3.2 mm Unipolar and Bipolar Pacemaker Leads and Connectors", Pace. vol. 9, pp. 1181-1185, Nov.-Dec. 1986, Part II; and International Standard IS-1, International Organization for Standardization document ISO/DIS 5841-3, 1989).

Various embodiments of the invention, including the preferred embodiment, further include at least one reinforcing structure on spring clip 8 to provide support for base portion 9 as well as additional spring force to accompany that of the spring members 12 and 14. FIGS. 2 through 4A illustrate one such reinforcing structure, comprising reinforcing flanges 2 and 4 carried by base portion 9 of the spring clip. As shown in FIG. 2, reinforcing flange 4 is formed from an edge portion of the base member 9 that is located alongside of the spring member 12. This edge portion is bent down along a bend line 27 so that the reinforcing flange 4 is disposed at a 90 degree angle to the plane of base member 9 and spring member 12. Likewise, reinforcing flange 2 is formed from an edge portion of the base member 9 that is located alongside of the spring member 14. This edge portion is bent down along a bend line 29 so that the reinforcing member 2 is disposed at a 90 degree angle to the plane of base member 9 and spring member 14. In some embodiments of the invention, the reinforcing flanges 2 and 4 may be bent at other angles. For example, the reinforcing members 2 and 4 may be bent at a 180 degree angle to fold back on the spring members 12 and 14. The reinforcing members 2 and 4 improve the functionality of the spring clip 8 by increasing the displacement of jaws 16 and 18 and increasing the spring force of the spring members 12 and 14 when a transverse compressing force, shown by an arrow 30 (see FIG. 4A), is applied to the leg portions 20 and 22 of the spring clip. Thus, the reinforcing members 2 and 4 allow the spring clip 8 to provide a larger opening of the jaws 16 and 18 to accept the terminal pin 6, with a smaller displacement of the leg members 20 and 22, than would be possible without the reinforcing members. The reinforcing members 2 and 4 intensify the displacement of the jaws 16 and 18 relative to the displacement of the leg members 22 and 24, while centering and supporting the spring clip 8. Furthermore, the reinforcing members 2 and 4 provide support for the spring members 12 and 14 to limit the stresses imposed upon the spring members 12 and 14 when a transverse compressing force 30 is applied to the leg members 20 and 22, thereby protecting the spring members 12 and 14 from fatigue.

In other embodiments of the invention, more or fewer reinforcing members 2 and 4 may be provided. Also, the reinforcing members may consist of a structure which is separate from the spring clip 8, rather than integral therewith, such as a plate or bar affixed to the spring clip by spot welding or other electrical or mechanical attachment means.

Figure 4B:
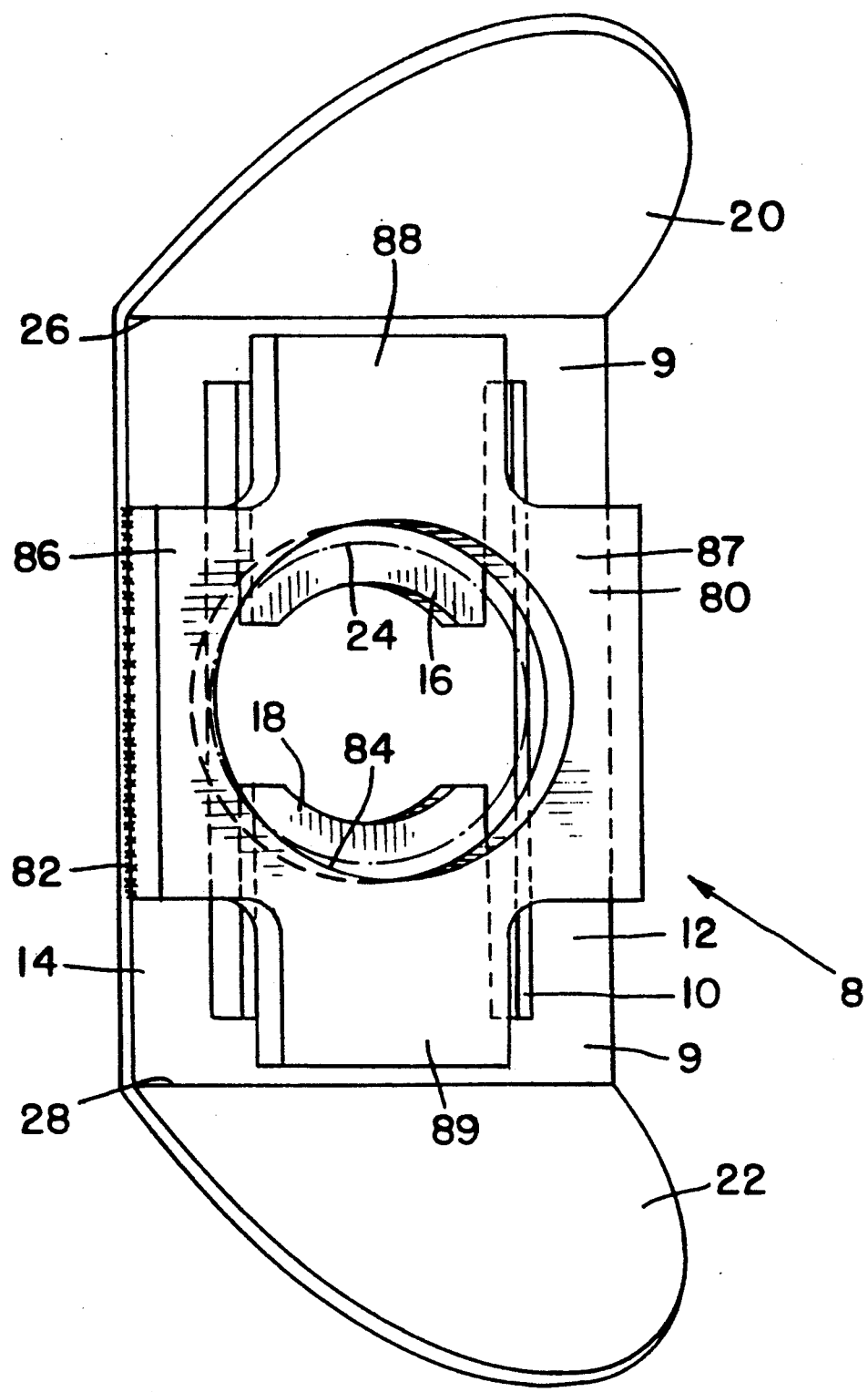
FIG. 4B is a perspective view of an inverted resilient metallic spring clip that is provided with a cross reinforcement bar.

One example of a reinforcing structure which is separate from the spring clip 8 is illustrated in FIG. 4B, which is a perspective view of an inverted resilient metallic spring clip 8 that is provided with a cross reinforcement bar 80. The cross reinforcement bar 80 is constructed from the same material as the spring clip 8 in the shape of a cross including reinforcement bar spring members 86 and 87 and reinforcement bar jaw members 88 and 89. The cross reinforcement bar 80 is perforated by a centrally located circular cross bar aperture 84. The reinforcement bar spring member 86 lies opposite the reinforcement bar spring member 87, across the circular cross bar aperture 84. Likewise, the reinforcement bar jaw member 88 lies opposite the reinforcement bar jaw member 89, across the circular cross bar aperture 84. The width of the reinforcement bar spring members 86 and 87 is somewhat smaller than the length of the spring members 12 and 14. The reinforcement bar jaw members 88 and 89 extend from the cross bar aperture 84 nearly to the bend lines 26 and 28, respectively, where the base portion 9 of the spring clip 8 intersects with the leg members 20 and 22. In a preferred embodiment of the invention which employs a cross reinforcement bar 80, the reinforcement bar spring members 86 and 87 are symmetric in form and identical in length and width and the reinforcement bar jaw members 88 and 89 are symmetric in form and identical in length and width. The lengths and widths of the reinforcement bar spring members 86 and 87 may take various proportions with respect to the lengths and widths of the reinforcement bar jaw members 88 and 80. The cross reinforcement bar 80 is attached to the spring clip 8 by means of welds, one of which is shown at 82, which attach the reinforcement bar spring members 86 and 87 to the spring members 14 and 12, respectively. In a preferred embodiment of the invention which employs a cross reinforcement bar 80, the cross bar aperture 84 has a diameter which is larger than the diameter of the central opening 24 (FIG. 5) of lumen 50.

The cross reinforcement bar 80 acts to magnify the motion of the jaws 16 and 18 when the leg members 20 and 22 are pressed inward. Because the width of the reinforcement bar spring members 86 and 87 is somewhat smaller than the length of the spring members 12 and 14, only corresponding portions of the spring members 12 and 14 are held firm when the leg members 20 and 22 are pressed inward. Thus complementary portions of the spring members 12 and 14 are free to flex, allowing opening movement of the jaws 16 and 18. The motion of the jaws 16 and 18 is further amplified by limiting the area of flexure where the base portion 9 of the spring clip 8 intersects with leg member 20 and where the base portion 9 intersects with leg member 22. The reinforcement bar jaw members 89 and 88, by extending to these lines of intersection (bend lines 26 and 28), provide a firm surface about which the spring clip 8 is flexed and effectively limit the area of flexure to additionally augment the motion of the jaws.

Referring to FIGS. 1 and 4A, the terminal pin 6 of a lead 7 may be inserted into the connector assembly 5 (FIG. 1) simply by pushing the proximal end of the lead into the lead cavity or lumen 50 of the connector assembly housing 102 (see FIGS. 5 and 6), using a negligible insertion force, represented by arrow 31 The jaws 16 and 18 will readily accommodate the inserted terminal pin 6 of lead 7 because the jaws 16 and 18 and the spring members 12 and 14 Can flex so as to not significantly oppose the entry of the terminal pin 6. No auxiliary equipment or tool is required to lock the terminal pin 6 into place and no action by the implanting physician is required other than to insert the terminal pin and lead fully into the connector assembly 5. The physician may, optionally, apply a small compressive force 30 to the leg members 20 and 22 to further facilitate entry of the pin 6 into the jaws of the spring clip but this is not required. In either event, after insertion of the terminal pin 6 into the spring clip 8 the spring clip automatically secures the terminal pin and lead to the assembly and provides electrical contact with the terminal pin.

If a force, shown by arrow 32, is applied directly to the lead 7 in a direction that would result in the lead's withdrawal from the connector assembly 5, the withdrawal force 32 causes the jaws 16 and 18 to tighten their grip on pin 6, thereby increasing the holding force 33 of the spring clip 8 on the pin 6. In this manner, the spring clip 8 responds to a withdrawal force 32 applied to the lead 7 by increasing the holding force 33 of the connector 5. Pulling on the lead 7 makes the clip 8 lock the pin tighter. To release the terminal pin 6 and lead 7 from the connector assembly 5, one may apply a transverse compressing force 30 to the legs 20 and 22, by squeezing opposite ends of the button 34 (FIGS. 1 and 5) toward one another, to squeeze the ends of the legs toward the pin 6, simultaneously flexing the jaws 16 and 18 and the spring members 12 and 14, opening the jaws 16 and 18 and relaxing the holding force 33 on the pin 6. No auxiliary equipment or tool is required to release the pin 6 and lead 7 from the connector assembly 5.

Referring now to FIGS. 1, 5, 6 and 7, the neck assembly 42 of stimulation device 1 includes an electrode lead receiving cavity 36 in the form of a stepped lumen 50 having a small diameter portion 51 at a closed innermost end thereof, a medially disposed medium diameter portion 52 and an outermost large diameter portion 53 extending to the opening 40 in the exterior housing 102 of the neck assembly. The housing 102 is preferably constructed from a plastic, silastic or other electrically non-conductive material, such as epoxy. The stepped lumen 50 is disposed between portions 44 and 46 of the housing 102. The stepped lumen 50, through opening 40, receives terminal pin 6 and the proximal end portion of electrode lead 7. As shown in the embodiment of FIG. 6, the neck assembly 42 may include two conductive connectors 64 and 66, for use with a bipolar electrode lead (not shown). Alternatively, in the embodiment of the invention shown in FIG. 5, the assembly 42 may include only one conductive connector 64, located within the small diameter portion 51 of the stepped lumen 50, for use with a unipolar electrode lead such as lead 7 (FIG. 1).

Referring to FIG. 6, conductive Connector 64 is located within the small diameter portion 51 of stepped lumen 50 while conductive connector 66 is located within the medium diameter portion 52 of the stepped lumen. The two conductive connectors 66 and 64 correspond, respectively, to connectors for a pacing ring electrode and a pacing tip electrode that are standard in the art of bipolar cardiac pacing. A plurality of sealing rings 60 and 62 are provided in each of lumen portions 51 and 52, respectively, to seal the stepped lumen 50 against body fluid encroachment and to isolate the conductive connectors 64 and 66 from one another.

The conductive connector 64 comprises the aforementioned resilient metallic spring clip 8, illustrated in isolation in FIGS. 2, 3 and 4A, including the two arm members 20 and 22, the two metallic jaws 16 and 18 bounded by the aperture 10, and the base member 9 and the two spring members 12 and 14 bordering the aperture 10. The spring members 12 and 14 are embedded within a resilient release button 34, preferably of silicone rubber, which extends through the entire thickness of housing 102 and adds stiffness and support to the spring members 12 and 14 to greatly improve the holding performance of the connector assembly 5. The two directly opposed jaws 16 and 18 are also partially embedded within the resilient release button 34 but extend therefrom to intrude into the small diameter portion 51 of the stepped lumen 50. Jaws 16 and 18 may be angled in the direction of the insertion (i.e., toward the closed end of the lumen) at a small angle, to aid terminal pin insertion. Upon insertion of a terminal pin into the lead receiving cavity 36, such that the terminal pin enters the small diameter portion 51 of the stepped lumen 50 and engages jaws 16 and 18, the jaws 16 and 18 deflect from the plane 72 to allow the terminal pin to fully penetrate the small diameter portion of the lumen.

The resilient release button 34 provides precise alignment of the spring clip 8 with respect to the stepped lumen 50. It also promotes stiffness of and support for the spring clip 8. Furthermore, the release button 34 forms a compliant seal with the connector housing 102 which effectively seals the connector housing against intrusion of body fluids and eliminates problems created by clogging blood within the housing. In addition, the release button 34 serves as an electrical insulator, that electrically separates the circuits internal to the case 100 of the stimulation device from the patient's body. Moreover, the resilient release button 34 creates a sealing surface within the stepped lumen 50, eliminating the need for sealing rings on terminal pin 6 and meeting a VS-1B standard in regard thereto.

The conductive connector 66, illustrated in FIG. 6, is composed of two electrically coupled conductive metallic cylinders 67 and 68, which are further electrically coupled to resilient metallic spring contacts 69. When the terminal pin of a bipolar implantable stimulation lead (not shown) is inserted into the stepped lumen 50, the spring contacts deflect within the medium diameter portion of stepped lumen 52 to admit the terminal pin and, in addition, make good electrical contact with a ring connector (not shown) on the terminal pin. At least one of the cylinders 67 and 68 makes an electrical connection with conductive wires (not shown) which connect the ring connector of the terminal pin to electrical circuits (not shown) within the Case 100 of the implantable stimulation device.

As indicated earlier, FIG. 1 is a perspective view of a single chamber implantable stimulator 1 embodying the connector assembly 5 of the present invention. The connector assembly 5 may be embodied in a single chamber pacemaker, a dual chamber pacemaker, antiarrhythmia pacers, defibrillators, cardiomyoplasty stimulators, neurostimulators and other implantable stimulators. In using the connector assembly 5, the terminal pin 6 of an electrode lead 7 is inserted into the opening 40 of the connector housing 102, into full engagement with the assembly 5, connecting the lead to the implantable stimulation device. To release the lead 7, the resilient release button 34 is simultaneously pressed on both sides of the neck assembly 42. In an alternative arrangement, it is possible to have a configuration which employs a single release button on one side of the connector housing 102.

It is apparent from the foregoing discussion that the present invention provides an improved self-locking connector assembly for an implantable stimulation device. The connector assembly responds to the application of a withdrawal force on an engaged lead by increasing its holding force on the lead. The connector assembly improves convenience to an implanting surgeon by requiring no manipulation of auxiliary devices or tools and by requiring the use of only a minimal insertion force to insert the terminal pin of the lead into the connector assembly to electrically connect the lead to the stimulation device. Removal of the lead from the connector assembly is easily accomplished by squeezing the release button and withdrawing the lead.

Although the invention has been described with reference to particular embodiments, it is to be understood that such embodiments are merely illustrative of the application of the principles of the invention. Numerous modifications may be made therein and other arrangements may be devised without departing from the true spirit and scope of the invention.

What is claimed is:

1. A connector assembly for detachably connecting a terminal pin of an electrical lead to an electrical device, comprising:
   a connector housing attached to said device, said connector housing having a lumen therein adapted to accept the terminal pin; and
   a resilient spring clip affixed within said connector housing and having a generally centrally located opening therethrough adapted to receive the terminal pin, said clip including at least two spring members and one pair of jaws bounding said opening, each jaw of said pair of jaws being positioned on an opposite side of said opening to its paired jaw, said jaws being adapted to fixably engage the terminal pin of the lead when the terminal pin is inserted into said opening, said jaws and said spring members being positioned within a plane perpendicular to a longitudinal axis of the lumen when in a relaxed condition, out of engagement with a terminal pin, said resilient spring clip further comprising two leg members extending distally from said jaws and bent to form a high angle with the plane of the jaws and the spring members, said leg members being adapted to translate a force to said jaws and spring members in response to an application of a transverse compressing force to said leg members to thereby release said jaws from the terminal pin of the lead.

2. A connector assembly for detachably connecting a terminal pin of a stimulating lead to an implantable stimulation device, comprising:
   a connector housing attached to said implantable stimulation device, said connector housing having a cylindrical lumen therein adapted to accept a terminal pin of a lead; and
   a resilient metallic spring clip affixed within said connector housing and having a generally centrally located opening therethrough adapted to receive the terminal pin, said spring clip including at least two metallic spring members and one pair of metallic jaws bounding said opening, said metallic jaws being positioned generally parallel to said spring members, each jaw of said pair of jaws being positioned on an opposite side of said opening to its paired jaw, said jaws being adapted to fixably engage the terminal pin when the terminal pin is inserted into said opening, said jaws and said spring members being positioned within a plane perpendicular to a longitudinal axis of the lumen when in a relaxed condition out of engagement with a terminal pin, said resilient metallic spring clip further comprising two leg members extending distally from said metallic jaws and bent to form a high angle the plane of the jaws and spring members, said leg members being adapted to translate a force to said jaws and spring members in response to an application of a transverse compressing force to said leg members to thereby release said jaws from the terminal pin of the lead.

3. A connector assembly according to claim 2, wherein said resilient metallic spring clip is composed of an electrically conductive material to electrically couple the connector assembly to the stimulating lead, the connector assembly further comprising an electrical conductor extending from said spring clip to said implantable stimulation device.

4. A connector assembly according to claim 2, further comprising at least one resilient release button of silicone rubber overlying said leg members and firmly embedding said leg members and spring members therein, said at least one button being adapted to seal said connector assembly from intrusion of body fluids.

5. A connector assembly according to claim 2, wherein said metallic spring clip is constructed of a single layer of sheet metal.

6. A connector assembly according to claim 2, wherein said metallic spring clip is constructed of a composite of multiple laminated leaves of sheet metal.

7. A connector assembly according to claim 2, wherein said jaws have end portions that are in the form of V-shaped teeth.

8. A connector assembly according to claim 2, wherein said jaws have end portions that are in the form of flat teeth.

9. A connector assembly according to claim 2, wherein said jaws have end portions that are internally radiused.

10. A connector assembly according to claim 2, wherein each of said jaws has an end portion that is in the form of multiple teeth.

11. A connector assembly according to claim 2, wherein the centrally located opening is generally in the form of an H-shape, said two metallic spring members extend parallel and peripherally to the legs of the H- shape, said one pair of metallic jaws extend from the top and bottom of the H-shape into the cross-bar of the H-shape, and each of said leg members extends from a respective metallic jaw above and below the H-shape.

12. A connector assembly according to claim 2, further comprising at least one reinforcing member affixed to said spring clip, said reinforcing member being aligned parallel to said at least two spring members.

13. A connector assembly according to claim 13, further comprising at least one resilient release button of silicone rubber overlying said leg members and firmly embedding said leg members and spring members therein, said at least one button being adapted to seal said connector from intrusion of body fluids.

14. A connector assembly according to claim 12, wherein said spring clip is composed of an electrically conductive material to electrically couple the connector assembly to said stimulating lead, the connector assembly further comprising an electrical conductor extending from said spring clip to said implantable stimulation device.

15. A connector assembly for detachably connecting a terminal pin of a stimulating lead to an implantable stimulation device, comprising:
  a connector housing attached to said implantable stimulation device, said connector housing having a cylindrical lumen therein adapted to accept a terminal pin of a lead; and
  a resilient metallic spring clip affixed within said connector housing and having a generally centrally located opening therethrough adapted to receive the terminal pin, said spring clip including at least two metallic spring members and one pair of metallic jaws bounding said opening, said metallic jaws being positioned generally parallel to said spring members, each jaw of said pair of jaws being positioned on an opposite side of said opening to its paired jaw, said jaws being adapted to fixably engage the terminal pin when the terminal pin is inserted into said opening and being adapted to increase the retaining force on the terminal pin upon application of a withdrawing force on the terminal pin, said metallic jaws and said spring members being positioned within a plane perpendicular to the longitudinal axis of the lumen when in a relaxed condition, out of engagement with a terminal pin, said resilient metallic spring clip further comprising two leg member extending distally from said metallic jaws and bent to form a high angle with the plane of the jaws and spring members, said leg members being adapted to translate a force to said jaws and spring members in response to an application of a transverse compressing force to said leg members to thereby release said jaws from the terminal pin of the lead.

16. A connector assembly according to claim 15, wherein said resilient metallic spring clip is composed of an electrically conductive material to electrically couple the connector assembly to the stimulating lead, the connector assembly further comprising an electrical conductor extending from said spring clip to said implantable stimulation device.

17. A connector assembly according to claim 15, further comprising at least one resilient release button of silicone rubber overlying said leg members and firmly embedding said leg members and spring members therein, said at least one button being adapted to seal said connector assembly from intrusion of body fluids.

18. A connector assembly according to claim 15, wherein said metallic spring clip is constructed of a single layer of sheet metal.

19. A connector assembly according to claim 15, wherein said metallic spring clip is constructed of a composite of multiple laminated leaves of sheet metal.

20. A connector assembly according to claim 15, wherein the centrally located opening is generally in the form of an H-shape, said two metallic spring members extend parallel and peripherally to the legs of the H-shape, said one pair of metallic jaws extend from the top and bottom of the H-shape into the cross-bar of the H-shape, and each of said leg members extends from a respective metallic jaw above and below the H-shape.

21. A connector assembly according to claim 15, further comprising at least one reinforcing member affixed to said spring clip, said reinforcing member being aligned parallel to said at least two spring members.

22. A connector assembly according to claim 21, further comprising at least one resilient release button of silicone rubber overlying said leg members and firmly embedding said leg members and spring members therein, said at least one button being adapted to seal said connector assembly from intrusion of body fluids, 23. A connector assembly according to claim 21, wherein said spring clip is composed of an electrically conductive material to electrically couple the connector assembly to said stimulating lead, the connector assembly further comprising an electrical conductor extending from said spring clip to said implantable stimulation device.

24. A connector assembly for detachably connecting a terminal pin of an electrical lead to an electrical device, comprising:
  a connector housing of insulating material carried by said electrical device, said housing including an elongate lumen therein having a closed proximal end and an open distal end which receives said electrical lead; and
  a generally U-shaped electrically conductive spring clip positioned within said housing and having first and second spaced apart leg portions extending alongside respective opposite sides of the lumen, a base portion extending between said leg portions generally transversely of the lumen, and first and second jaw members extending generally toward one another transversely of the lumen and having end portions thereon terminating at spaced apart locations within the lumen, the spacing between said end portions being less than the width of the terminal pin so that said jaw members are adapted to grip the terminal pin upon insertion of the terminal pin into the lumen, said U-shaped spring clip and said housing being constructed and arranged so that upon application of a compressive force to opposite sides of the housing, adjacent to said first and second leg portions, said first and second jaw members move away from one another, increasing the separation of the end portions thereof to a spacing greater than the width of the terminal pin and facilitating withdrawal of the terminal pin from the lumen.

25. A connector assembly according to claim 24, wherein said leg portions, said base portion and said jaw members are integral with one another.

26. A connector assembly according to claim 24, wherein said lumen has a circular cross-section.

27. A connector assembly according to claim 24, wherein said jaw members are carried by said base member and are coplanar with said base member when said spring clip is in a relaxed condition, out of engagement with a terminal pin, and wherein said jaw members flex out of the plane of said base member when engaged by a terminal pin.

28. A connector assembly according to claim 27, wherein said jaw members grip the terminal pin with a retaining force when engaged by the terminal pin, and wherein, in the absence of a compressive force on said leg portions, said retaining force increases upon application of a withdrawing force to the terminal pin.

29. A connector assembly according to claim 28, wherein said base member includes a pair of integral reinforcing flanges positioned perpendicularly to the plane of said base member and in spaced apart relation to one another.

30. A connector assembly according to claim 28, further comprising a cross-shaped reinforcement bar positioned in a plane parallel and adjacent to said spring clip base portion and having the lumen extending therethrough, including two reinforcement bar spring members extending opposite the lumen generally perpendicular to said spring members and two reinforcement bar jaw members extending opposite the lumen generally parallel to said jaw members, said reinforcement bar spring members being firmly affixed to said spring members.

31. A connector assembly according to claim 30, wherein said reinforcement bar jaw members extend outward from the lumen substantially to the intersections of said spring clip base portion and said leg portions.

32. A connector assembly according to claim 30, wherein the length of said spring members extend beyond the width of said reinforcement bar spring members.

* * * * *